United States Patent [19]

Campbell et al.

[11] Patent Number: 5,342,313

[45] Date of Patent: * Aug. 30, 1994

[54] FLUID PUMP FOR A FLEXIBLE, VARIABLE GEOMETRY RESERVOIR

[75] Inventors: Robert E. Campbell, Chicago, Ill.; Andre A. Kulisz; Valery Migachyov, both of St. Paul, Minn.

[73] Assignee: Infusion Technologies Corporation, Minnetonka, Minn.

[*] Notice: The portion of the term of this patent subsequent to Aug. 3, 2010 has been disclaimed.

[21] Appl. No.: 970,104

[22] Filed: Nov. 2, 1992

[51] Int. Cl.⁵ .................................................. A61M 1/00
[52] U.S. Cl. .................................. 604/153; 604/132; 222/103
[58] Field of Search ................. 604/67, 131, 132, 153; 222/103

[56] References Cited

U.S. PATENT DOCUMENTS

| | | |
|---|---|---|
| D. 294,733 | 3/1988 | Peterson et al. |
| 2,761,445 | 9/1956 | Cherkin |
| 2,849,159 | 8/1958 | Kaufmann |
| 3,151,616 | 10/1964 | Selfon ............................ 604/131 |
| 3,198,385 | 8/1965 | Maxwell |
| 3,565,292 | 2/1971 | Jinotti ............................. 222/146 |
| 3,625,401 | 12/1971 | Terry ............................. 222/103 |
| 3,640,277 | 2/1972 | Adelberg |
| 3,701,345 | 10/1972 | Hellman et al. |
| 3,884,228 | 5/1975 | Hahn |
| 3,901,231 | 8/1975 | Olson |
| 3,907,504 | 9/1975 | Hammond et al. |
| 4,033,479 | 7/1977 | Fletcher et al. ................... 222/61 |
| 4,038,983 | 8/1977 | Mittleman et al. |
| 4,155,362 | 5/1979 | Jess |
| 4,157,771 | 6/1979 | Smith |
| 4,210,138 | 7/1980 | Jess et al. |
| 4,213,454 | 7/1980 | Shim |
| 4,278,085 | 7/1981 | Shim |
| 4,299,218 | 11/1981 | Knigge et al. |
| 4,335,835 | 6/1982 | Beigler et al. |
| 4,337,769 | 7/1982 | Olson |
| 4,346,705 | 8/1982 | Pekkarinen et al. |
| 4,396,385 | 8/1983 | Kelly et al. .................... 604/152 |
| 4,416,595 | 11/1983 | Cromie ........................... 417/476 |
| 4,443,218 | 4/1984 | DeCant, Jr. et al. ............... 604/67 |
| 4,447,224 | 5/1984 | DeCant, Jr. et al. ............... 604/67 |
| 4,504,200 | 3/1985 | Olson .............................. 417/476 |
| 4,504,265 | 3/1985 | Rudzena et al. ................... 604/86 |
| 4,505,701 | 3/1985 | Navato ........................... 604/143 |
| 4,539,005 | 9/1985 | Greenblatt ....................... 604/141 |
| 4,559,038 | 12/1985 | Berg et al. ....................... 604/153 |
| 4,613,327 | 9/1986 | Tegrarian et al. ................. 604/141 |
| 4,626,243 | 12/1986 | Singh et al. ...................... 604/141 |
| 4,634,430 | 1/1987 | Polaschegg ...................... 604/141 |
| 4,650,469 | 3/1987 | Berg et al. ....................... 604/131 |
| 4,673,391 | 6/1987 | Kondo et al. .................... 604/141 |
| 4,731,058 | 3/1988 | Doan ............................... 604/155 |
| 4,741,736 | 5/1988 | Brown ............................. 604/134 |
| 4,767,406 | 8/1988 | Wadham et al. ................. 604/155 |
| 4,823,833 | 4/1989 | Hogan et al. ..................... 137/567 |
| 4,840,017 | 6/1989 | Miller et al. ....................... 53/468 |

(List continued on next page.)

FOREIGN PATENT DOCUMENTS

| | | | |
|---|---|---|---|
| 248538 | 12/1987 | European Pat. Off. ............ 604/131 |
| 0416495A2 | 3/1991 | European Pat. Off. |
| 2603488 | 3/1988 | France ........................... 604/131 |

*Primary Examiner*—John G. Weiss
*Attorney, Agent, or Firm*—Jones, Day, Reavis & Pogue

[57] ABSTRACT

A positive displacement infusion pump for delivery of intravenous fluid at a predetermined rate from a standard, flexible intravenous bag to a patient. The pump includes a bag chamber with a moveable side opposing a stationary side. The bag chamber has a volume which is greater than that of the bag so the bag may be easily inserted into the chamber. The moveable side is controlled such that adjustments are made to the reduction of the chamber volume and/or rate of reduction of the chamber volume to precisely control the fluid flow out of the bag in accordance with information in the computer memory.

22 Claims, 7 Drawing Sheets

U.S. PATENT DOCUMENTS

| | | | |
|---|---|---|---|
| 4,854,324 | 8/1989 | Hirschman et al. | 128/655 |
| 4,880,414 | 11/1989 | Whipple | 604/283 |
| 4,898,578 | 2/1990 | Rubalcaba, Jr. | 604/66 |
| 4,898,583 | 2/1990 | Borsanyi et al. | 604/153 |
| 4,898,584 | 2/1990 | Borsanyi et al. | 604/153 |
| 4,898,585 | 2/1990 | Borsanyi et al. | 604/153 |
| 4,905,698 | 3/1990 | Strohl, Jr. et al. | 128/655 R |
| 4,915,688 | 4/1990 | Bischof, deceased et al. | 604/83 |
| 4,915,693 | 4/1990 | Hessel | 604/132 |
| 4,919,650 | 4/1990 | Feingold et al. | 604/67 |
| 4,929,243 | 5/1990 | Koch et al. | 604/283 |
| 4,931,041 | 6/1990 | Faeser | 604/155 |
| 4,952,205 | 8/1990 | Mauerer et al. | 604/67 |
| 4,963,133 | 10/1990 | Whipple | 604/283 |
| 4,979,940 | 12/1990 | Bobo, Jr. et al. | 604/50 |
| 4,991,743 | 2/1991 | Walker | 604/132 |
| 5,000,739 | 3/1991 | Kulisz et al. | 604/132 |
| 5,053,031 | 10/1991 | Borsanyi | 604/891.1 |
| 5,098,377 | 3/1992 | Borsanyi et al. | 604/30 |
| 5,104,374 | 4/1992 | Bishko et al. | 604/31 |
| 5,135,646 | 8/1992 | Tanokura et al. | 222/103 |
| 5,168,892 | 12/1992 | Sunderland | 604/153 |
| 5,232,439 | 8/1993 | Campbell et al. | 604/132 |

FLUID PUMP FOR A FLEXIBLE, VARIABLE GEOMETRY RESERVOIR

BACKGROUND OF THE INVENTION

The present invention relates to systems for administering intravenous (IV) fluid. In particular, the present invention relates to a positive displacement infusion pump for delivering a predetermined rate of flow of an IV fluid from a standard flexible intravenous bag to a patient.

Intravenous injection of medicating, nourishing, hydrating or electrolyte replacing fluids is an essential method for treating various medical conditions. For instance, the treatment of chronic bacterial infections, hematological disorders, intestinal disorders, cancer and chronic pain often require a continuous or recurring delivery of solutions by IV injection. The IV solutions are pharmacologically prepared within a flexible bag. Traditionally, such treatments have been administered in a medical facility because of the equipment required to deliver the IV solution, and because of the medical personnel required to monitor the administration of the treatment. As a result of growing medical costs, however, there has been a growing need to provide a relatively inexpensive IV fluid delivery system for home use which is ambulatory (i.e., portable), relatively simple to use, and is capable of accurately and dependably delivering an IV solution at a desired, predetermined and variable rate.

SUMMARY OF THE INVENTION

The present invention is a positive displacement infusion pump for delivering a predetermined rate of flow of an intravenous fluid from a standard flexible intravenous bag to a patient.

The infusion pump of the present invention includes a bag chamber for holding a standard, flexible, fluid-filled intravenous bag. The bag chamber, which includes a moveable member and a stationary side opposite the moveable member, has an initial volume which is the largest when the moveable member is in a starting position. Generally, the bag chamber is sized to urge the bag to conform to the shape of the bag chamber such that when the moveable member moves toward the stationary side at a predetermined rate, a predetermined volume of fluid is expressed out of an outlet of the bag.

Due to the geometry of the bag, however, when the bag chamber is at its initial volume, a contact area between a surface of the bag, the moveable member and the stationary side is relatively small. As the moveable member moves toward the stationary side, the contact area increases. Moreover, the volume of the chamber is greater than the volume of the bag and the relationship between the volumes changes non-linearly as the volume of the chamber is reduced. In order to express fluid out of the bag outlet at a predetermined rate, the rate at which the moveable member moves toward the stationary side must be adjusted downward as the contact area increases or chamber volume decreases.

Control means controls the rate of movement of the moveable member toward the stationary side. This rate adjustment is determined according to a parameter related to the position of the moveable member that, when moved, results in variation in contact area, and a predetermined fluid delivery rate. The control means thereby allows the infusion pump of the present invention to deliver a predetermined rate of fluid flow from the bag despite the changing contact area or chamber/bag volume relationship.

In a preferred embodiment, the moveable member is pivotally connected to the stationary side. The angular position of the moveable member relative to the stationary side bears a relationship to the size of the area contacted by the sides and to the relationship of the volume of the chamber to the volume of the bag. To express a constant predetermined volume of fluid out of the bag outlet at the predetermined rate, the control means determines the angular position of the moveable member relative to the stationary side (and hence the contact area and volume and rate relationships). The control adjusts the output signal to the motor to adjust the rate of movement of the moveable member as the moveable member approaches the stationary side in order to accurately control fluid flow.

DETAILED DESCRIPTION OF THE PREFERRED EMBODIMENTS

Figure 1:
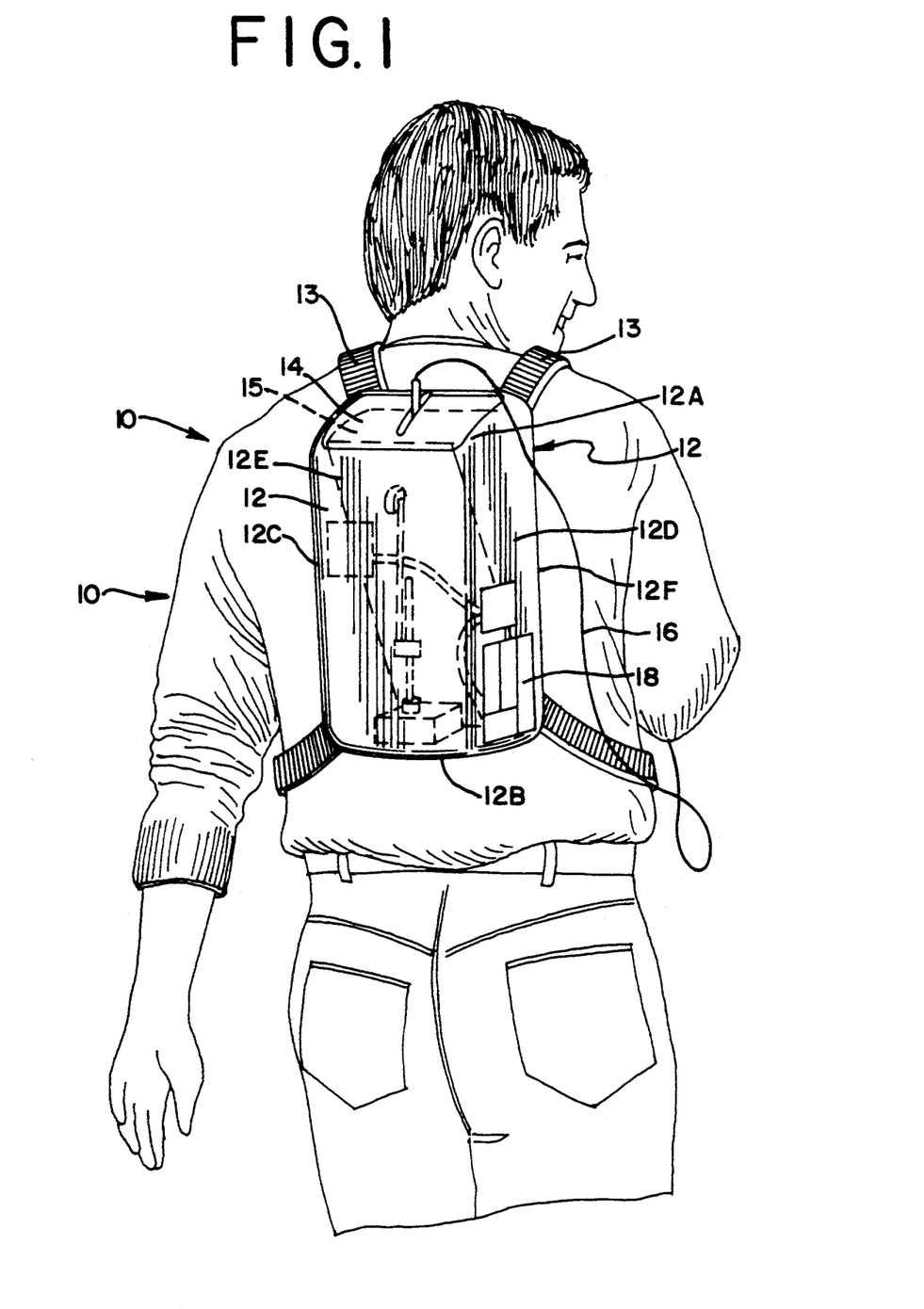
FIG. 1 is an rear elevational view of the preferred embodiment of the portable pump system being worn by a patient.

FIG. 1 shows the preferred embodiment of backpack-type portable pump system 10 being carried by a patient. System 10 generally includes container 12 and carrier straps 13. Container 12 is designed to be carried on the back of a patient with straps 13 positioned over the shoulders of the patient. Container 12 provides a discrete means for transporting pump system 10, which allows a patient to lead a relatively normal public life.

Container 12 includes top 12A, bottom 12B, left side wall 12C, right side wall 12D, back wall 12E and front wall 12F. Removable cover 14 in top 12A exposes an interior of container 12 for receiving and holding flexible intravenous bag 15 (shown in phantom). Connected to bag 15 is catheter 16, which carries fluid from bag 15 to the vascular system of the patient when pump system 10 is operating. User interface 18 is provided in right side wall 12D to select IV delivery parameters (such as flow rate in cc/hour or ml/hour) according to the prescribed needs of a patient, and to monitor operation of pump system 10.

Figure 2:
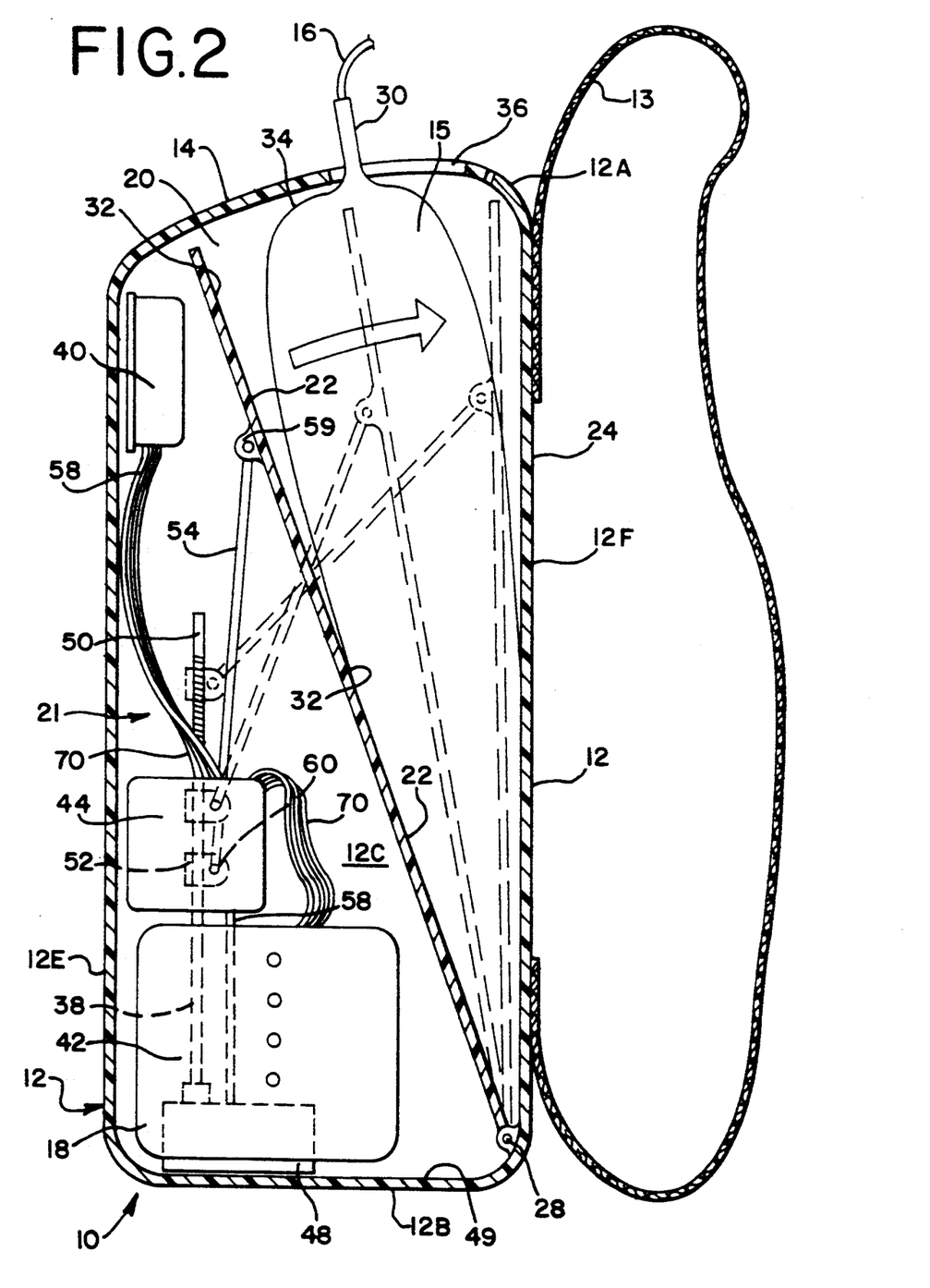
FIG. 2 is a cross-sectional view of the preferred embodiment of the present invention.

FIG. 2 is a cross-sectional view of container 12 of the preferred embodiment of FIG. 1. Container 12 generally includes bag chamber 20, pump drive 21 and moveable plate 22, which separates bag chamber 20 from pump drive 21.

Bag chamber 20, which is generally triangular shaped in cross section, is formed by stationary front wall 12F, removable cover 14 of container 12, moveable plate 22 and opposing side walls 12C and 12D. Side walls 12C and 12D are perpendicular to stationary front wall 12F and moveable plate 22 and serve to constrain bag 15. In one embodiment, bag chamber 20 has a maximum volume which is capable of holding bag 15 when it contains up to 3 liters of fluid. Front wall 12F is rigid and provides a surface against which IV bag 15 is compressed during operation of pump system 10.

Moveable plate 22 is pivotally connected to front wall 12F by hinge 28. Moveable plate 22 has a width which is approximately equal to a width of bag chamber 20, and which is slightly less than a width of bag 15. This tends to urge bag 15 to conform as much as possible to the shape of bag chamber 20. Moveable plate 22 includes bag contact surface 32 which contacts and squeezes bag surface 34, to force fluid contained within bag 15 out bag outlet 30 to catheter 16.

Removable cover 14 is provided with opening 36 to accommodate the change in position of bag outlet 30 as a result of moveable plate 22 moving toward stationary front wall 12F of container 12.

Pump drive 21 is comprised of motor drive 15, assembly 38, controller 40, user interface 18, and power supply 44. Motor drive assembly 38 is provided to drive moveable plate 22 toward front wall 12F of container 12. Motor drive assembly 38 includes electric motor 48, lead screw 50, follower 52, and push rod 54.

Motor 48 is securely mounted to inner surface 49 of bottom 12B, with lead screw 50 oriented vertically toward cover 14. Motor 48, which communicates with controller 40 by electrical connection 59, is preferably a stepper motor. Motor 48 is capable of driving lead screw 50 one increment for each step command pulse provided to motor 48. A result of a continuing rotation of a magnet of motor 48 subsequent to each step command pulse, motor 48 also generates an electromagnetic field ("back emf") back to controller 40 via connection 59. The lead screw 50 includes external threads which are mated to internal threads of follower 52. As motor 48 rotates lead screw 50, follower 52 moves linearly along lead screw 50.

Push rod 54 is pivotally connected to moveable plate 22 at plate connection 58 and to follower 52 at follower connection 60. The linear movement of follower 52 along lead screw 50 away from motor 48 causes push rod 54 to force moveable plate 22 toward stationary front wall 12F. Conversely, as follower 52 moves toward motor 48 (i.e., when lead screw 50 rotates in an opposite direction), push rod 54 applies a negative force to moveable plate 22 which pulls moveable plate 22 away from front wall 12F.

Push rod 54 has a length greater than the distance between lead screw 50 and front wall 12F to ensure that movement of follower 52 away from motor 48 will always result in a positive application of force to moveable plate 22. This also ensures that fluid always flows only from bag 15 to the patient. Motor 48 will not inadvertently counter-rotate the lead screw 50, such as in the unlikely event of an electrical failure. In the event of such a failure, therefore, moveable plate 22 will be immobilized in order to keep a positive pressure on surface 34 bag 15. This ensures that no fluid flow from the patient to bag 15 will occur.

Pivotally connecting the bottom of moveable plate 22 to front wall 12F provides significant mechanical advantages. First, the pivotal arrangement at the bottom intersection of the moveable plate 22 to front wall 12F allows easy insertion of the bag. The bag may be simply placed into the triangular shaped chamber 20; the force of gravity assures that the bag settles in the lowest point, contacting both the moveable plate 22 and front wall 12.

Figure 3:
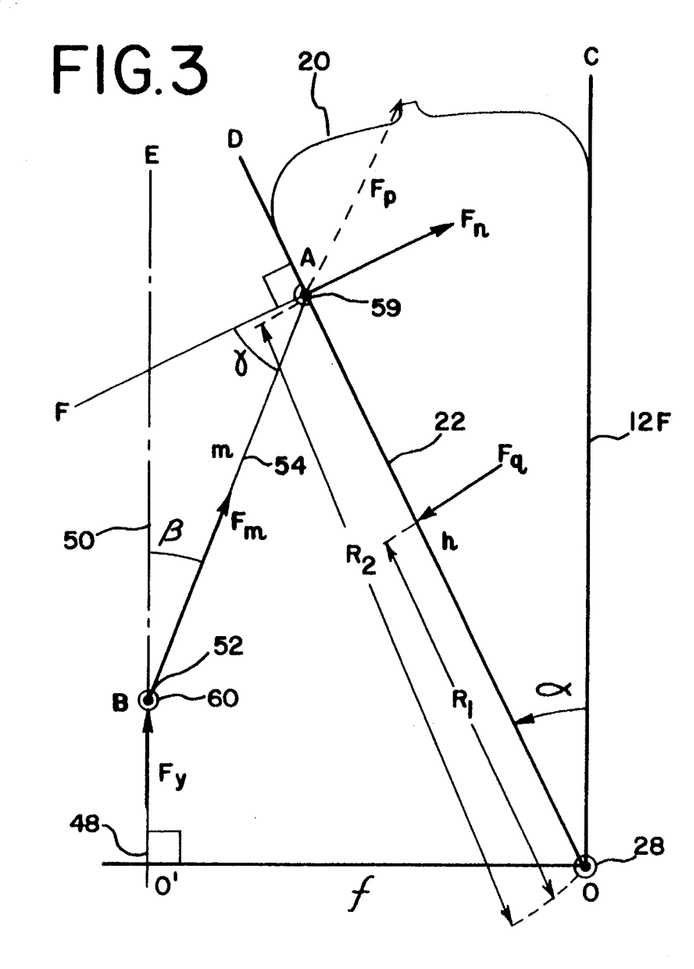
FIG. 3 is a schematic representation of the chamber and reservoir of the preferred embodiment.

Secondly, the pivotal arrangement provides a mechanical leverage arrangement. Application of a force at the plate connection 59, relatively high on the moveable plate 12, provides an increased force at points along the plate between it and hinge 28. The relative forces are illustrated in FIG. 3. For the plate, the moment $F_n R_2$ must equal the moment $F_q R_1$ where the system is in an equilibrium state.

$$F_n R_2 = F_q R_1 = R_2 F_y \frac{\cos\gamma}{\cos\beta} \quad \text{(Eq. 1)}$$

therefore, $$\frac{F_y}{F_q} = \frac{R_1 \cos\beta}{R_2 \cos\gamma} \quad \text{(Eq. 2)}$$

which represents the mechanical advantage.

There are two sources for this advantage:

For the pivotal plate:

$$F_q = \frac{F_n \cdot R_2}{R_1} \quad \text{(Eq. 3)}$$

To deliver the fluid, $F_n \cdot R_2 > F_q \cdot R_1$.

While, for the arm assembly:

$$F_n = F_y \cdot \frac{\cos\gamma}{\cos\beta} \quad \text{(Eq. 4)}$$

such that $F_n > F_y$ if $\cos\gamma/\cos\beta > 1$. Thus, the mechanical advantage increases when such mechanical advantage is most needed. As the moveable plate moves toward the stationary wall $\beta$ increases and $\gamma$ decreases, resulting in the increase of $\cos\gamma/\cos\beta$ and an increase in $F_n$ as compared to $F_y$. Thus, the V-shaped pivotal arrangement is particularly well suited for receiving the bag and for taking advantage of both leverage type mechanical arrangements for the moveable plate 22 and the push rod 54—follower 52—lead screw 50 configuration.

Controller 40 is preferably programmable digital circuitry which provides a step pulse output to motor 48 based upon flow rate inputs received from input user interface 18. Controller 40 regulates the frequency of the step pulse output to motor 48. Each step pulse from controller 40 corresponds to a known step advancement of motor 48. Controller 40 includes a counter or other memory device which records the number of step pulses provided to motor 48. The number of step pulses (and therefore the number of steps of motor 48) indicates the angular distance travelled by moveable plate 22.

Controller 40 implements (preferably by programmable logic) an algorithm for determining angular position of moveable plate 22, and therefore the contact area between bag surface 34, moveable plate 22 and front wall 12F, as a function of the number of steps of motor 48 recorded. Controller 40 determines, on a pulse-bypulse basis, the frequency of pulses supplied to motor 48. The rate of pulses supplied to motor 48 varies as moveable plate 22 moves toward front wall 12F and the area of contact increases between bag surface 34, moveable plate 22 and front wall 12F. For each step pulse output, controller 40 determines the time to the next pulse output based upon the number of pulses recorded (i.e., angular position of plate 22) and the selected flow rate.

User interface 18 provides inputs to controller 40 through cable 70 to select the flow rate provided by controller 40. Input parameters such as flow rate, ramp-up time, ramp-down time, system prime or other parameters are provided to controller 40 by programming switches 42A (shown in FIG. 6). Programming switches 42A are preferably binary decimal switches or keys, thumb-wheel switches, or any other suitable programming means compatible with programmable digital circuitry. User interface 18 also includes diagnostic display lights 42B and audio transducer 42C (shown in FIG. 6), which provide feedback information from controller 40 that is related to performance of pump system 10.

Power supply 44 is electrically connected to controller 40 for energizing pump system 10. In a preferred embodiment, power source 44 includes four AA batteries which are capable of operating pump system 10 for one complete IV delivery.

Figure 4A:
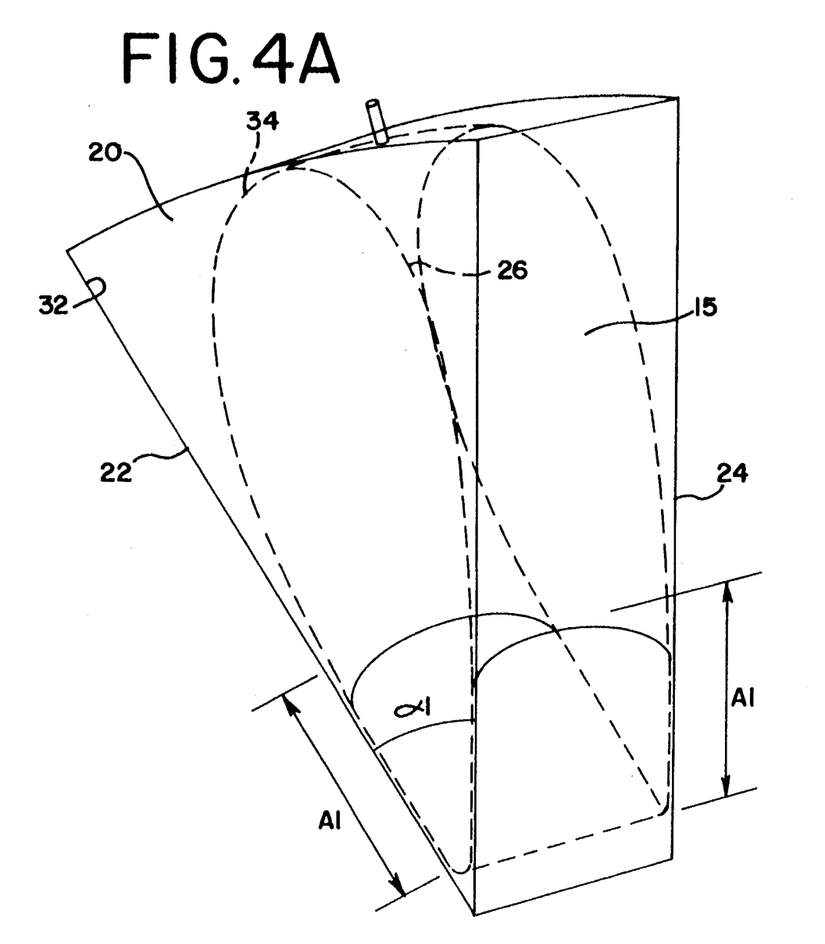
FIGS. 4A-4B are schematic representations of the chamber and reservoir of the preferred embodiment.
Figure 4B:
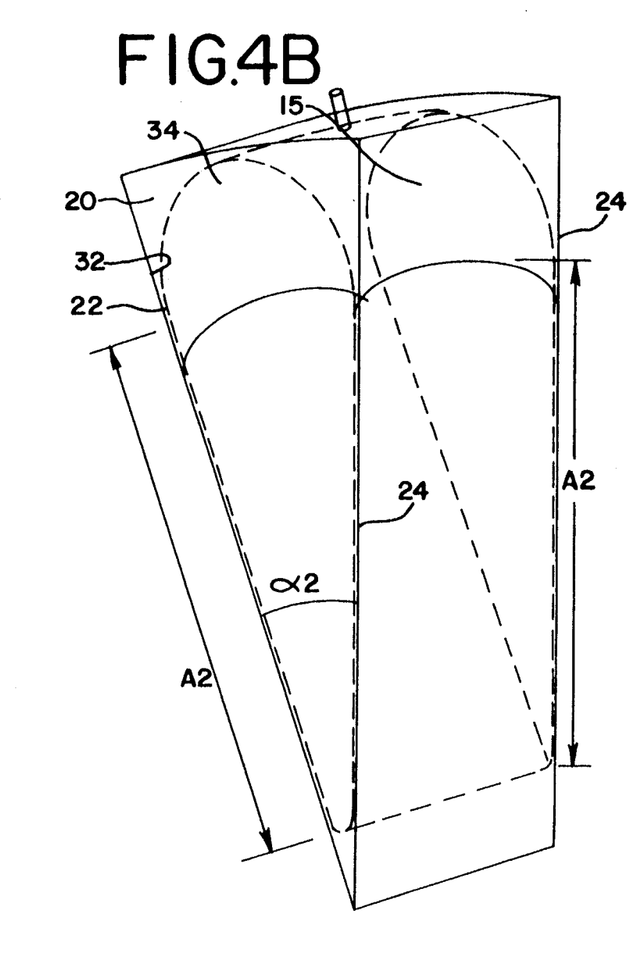

FIGS. 4A and 4B are graphical representations of the concept upon which the present invention is based. The present invention is based upon the recognition that the area of contact between bag surface 34, moveable plate 22 and front wall 12F, and the relationship of the volume of the chamber to the volume of the reservoir and their respective rates of reduction, varies during movement of plate 22. Therefore, in order to express a predetermined volume of fluid from intravenous bag 15 at a predetermined rate, the rate of movement of plate 22 must compensate for these nonlinear relationships.

As shown in FIG. 4A, when intravenous bag 15 is initially placed within bag chamber 20, bag surface 34 contacts front wall 12F and bag contact surface 32 of moveable plate 22. In the preferred embodiment, a beginning contact area A1 between bag surface 34, moveable plate 22 and front wall 12F is determined when moveable plate 22 is actuated until fluid is forced completely through catheter 16. Beginning contact area A1 corresponds to beginning angle $\alpha$ between moveable plate 22 and front wall 12F. As moveable plate 22 is actuated by motor drive assembly 38, an incremental movement of moveable plate 22 from angle $\alpha 1$ toward front wall 12F forces an incremental volume of fluid from bag 15. That incremental volume is a function of contact area A1 and the distance which moveable plate 22 moves toward front wall 12F.

As shown in FIG. 4B, as moveable plate 22 is actuated toward front wall 12F of container 12 by motor assembly 38, moveable plate 22 and front wall 12F contact a larger area of bag surface 34, as shown by contact area A2. Contact area A2 likewise corresponds to reduced angle $\alpha 2$ between moveable plate 22 and front wall 12F.

At angle $\alpha 2$, the contact area A2 is larger than A1. The same incremental movement of plate 22 from angle $\alpha 2$, therefore, forces a larger volume of fluid from bag 15. In order to express a constant predetermined volume of fluid out of bag 15 at a constant predetermined rate, controller 40 reduces the rate of movement of motor 48 (and hence of plate 22) to compensate for the increase in contact area.

Referring again to FIG. 3, bag chamber 20 is defined by the intersection of line C0, which represents front wall 12F, and line D0, which represents moveable plate 22. Point 0 represents the location of hinge 28. The angular distance between moveable plate 22 and front wall 12F is represented as angle $\alpha$.

Line 00' represents the linear distance of motor 48 from front wall 12F, which is represented by f. Point 0' indicates the position of motor 48 with line E0' representing lead screw 50. Line E0' is perpendicular to line 00' and parallel to line C0.

Line AB represents push rod 54, where point A represents plate connection 59 and point B represents follower 52 and follower connection 60. The distance between plate connection 59 (point A) and hinge 28 (point 0) is represented as h, and the distance between plate connection 59 and follower connection 60 is shown by m.

As motor 48 rotates lead screw 50, the rotational force of lead screw 50 is converted by follower 52 to a linear force in the direction $0' \rightarrow B$, as shown by force vector $F_y$. Linear movement of follower 52 along lead screw 50 results in a linear force in the direction $B \rightarrow A$, as indicated by force vector $F_m$. The angular distance of push rod 54 (line AB) from lead screw 50 (line E0') is shown by angle $\beta$.

The force applied by push rod 54 to moveable plate 22 at plate connection 59 provides a rotational force component, shown by force vector $F_n$, which moves moveable plate 22 toward front wall 12F. Force vector $F_n$ is perpendicular to moveable plate 22, with line AF representing an imaginary extension of force vector $F_n$ toward lead screw 50. The angular distance between push rod 54 and line AF is indicated by angle $\gamma$.

As has been stated:

$$A0 = h, \ AB = m, \ and \ 00' = f \qquad (Eq.\ 5)$$

In the preferred embodiment:

$$m > f \qquad (Eq.\ 6)$$

It is known that:

$$F_n = F_y \cdot \frac{\cos\gamma}{\cos\beta} \qquad (Eq.\ 7)$$

where, $$\cos\gamma = \sin\alpha \cdot \frac{\sqrt{m^2 - (f - h \cdot \sin\alpha)^2}}{m} + \cos\alpha \cdot \frac{(f - h \cdot \sin\alpha)}{m} \qquad (Eq.\ 8)$$

and, $$\cos\beta = \frac{\sqrt{m^2 - (f - h\sin\alpha)^2}}{m} \qquad (Eq.\ 9)$$

A ratio can be stated such that:

$$\overline{F}_n = \frac{F_n}{F_y} = \frac{\cos\gamma}{\cos\beta} \qquad (Eq.\ 10)$$

The following can also be stated:

$$\bar{F}_n = \sin\alpha + \cos\alpha \cdot \frac{(f - h \cdot \sin\alpha)}{\sqrt{m^2 - (f - h \cdot \sin\alpha)^2}} \quad \text{(Eq. 11)}$$

$$\bar{F}_{nmax} = \bar{F}_n(o) = \frac{f}{\sqrt{(m^2 - f^2)}} \quad \text{(Eq. 12)}$$

$$M_o = F_n \cdot h \cdot \frac{\cos\gamma}{\cos\beta} \quad \text{(Eq. 13)}$$

For the purpose of illustration, let h=250, f=150 and m=160. The following is then obtained:

TABLE 1

| α | sin α | cos α | (f − h sin α) | $\bar{F}_n$ |
|---|---|---|---|---|
| 0° | 0 | 1 | 150 | 2.69 |
| 5° | 0.087 | 0.996 | 128.2 | 1.42 |
| 10° | 0.174 | 0.985 | 106.5 | 1.05 |
| 20° | 0.342 | 0.940 | 64.5 | 0.756 |
| 30° | 0.5 | 0.866 | 25 | 0.637 |

The programmable controller 40 activates the frequency of pulses to the motor 48 in order to compensate for the difference between the volume reduction of the chamber 20 and the corresponding volume reduction of the bag 15, and the nonlinear variation of that relationship as the moveable plate 22 approaches the front wall 12F and the volume of the chamber is reduced. The volume of fluid expressed from the bag 15 equals the reduction in bag volume and, in turn, the rate of fluid expressed from the bag equals the rate the bag volume is reduced. Control of the volume reduction and rate of volume reduction of the bag within a volume-reducible chamber is addressed as part of the present invention.

If the chamber volume is represented by σ, the incremental change of the volume at a given position of the approach of moveable plate 22 to front wall 12F is represented by dσ. If the volume of the bag is represented by V, the incremental change of the volume at a given position of the approach of moveable plate 22 to front wall 12F is represented by dV.

The value of dσ is a function of dV:

$$d\sigma = dV \cdot S_\sigma \quad \text{(Eq. 14)}$$

where $S_\sigma$ is the relationship of bag volume reduction to chamber volume reduction at chamber volume σ. $S_\sigma$ is determined empirically, mathematically or by a combination of empirical observation and mathematical calculations.

The controller 40 has a memory which can store the values of the change in bag volume dV to obtain the desired delivery of fluid to the patient and stores the predetermined values $S_\sigma$ for the moveable plate 22 movement. The controller calculates dσ from the values of dV (which is the desired volume to be expressed from the bag 15) and $S_\sigma$ in its memory for a given position σ and actuates the motor to reduce the volume of the chamber dσ to accomplish dV, the volume of fluid expressed from the bag 15 and to the patient.

For example, with moveable plate 22 having length of 34 centimeters, width of 17 centimeters (resulting in plate area of 578 square centimeters), and initial bag volume of 3000 milliliters, the following relationship was determined:

TABLE 2

| ANGLE γ (FIG. 3) | TOTAL DELIVERED VOLUME | MOTOR STEP NUMBER | TOTAL RETAINED VOLUME | TOTAL CHAMBER VOLUME | CHAMBER TO BAG VOLUME RATIO | $S_\sigma$ |
|---|---|---|---|---|---|---|
| 25.5 | 0 | 76000 | 3000 | 3818 | 1.27 | — |
| 20 | 290 | 64750 | 2710 | 3158 | 1.17 | 2.28 |
| 15 | 740 | 52400 | 2260 | 2457 | 1.09 | 1.56 |
| 10 | 1420 | 38340 | 1580 | 1680 | 1.06 | 1.14 |
| 5 | 2180 | 21000 | 820 | 853 | 1.04 | 1.09 |
| 0 | 3013 | 800 | −13 | 0 | 1.00 | 1.02 |

The six sets of values in Table 2 are representative only; in actual use hundreds of values would be determined so that optimal precision in volume and rate of fluid delivery would be obtained. The indexing of the $S_\sigma$ values to the ending chamber volume σ (γ=20 degrees for $S_\sigma$ of 2.28, γ=15 degrees for $S_\sigma$ of 1.56, etc.), while a gross approximation here, would be much more accurate when hundreds of values between 25.5 degrees and 0 degrees are used.

Determining $S_\sigma$ for the entire range of moveable plate 22 movement and the desired volume of fluid dV to be delivered at that point in position and time allows the dσ, the change in chamber volume, i.e., the number of steps of the motor, to be determined. This allows for a predetermined, varying rate of flow to be accomplished with a relatively high degree of precision.

A similar calculation can be accomplished in the controller directly for rate of fluid flow by factoring in a time parameter. The rate of chamber volume reduction can be expressed by the change in chamber volume dσ divided by the corresponding change in time dt.

$$\frac{d\sigma}{dt} = R_i \cdot S_R \quad \text{(Eq. 15)}$$

where $R_i$ is the incremental rate of fluid flow expressed from the bag 15 at specific chamber volume σ and $S_R$ is the relationship of rate of chamber volume reduction to fluid flow $R_i$. The memory of the controller 40 contains both the predetermined $S_R$ values for the various chamber volumes σ and $R_i$ is the desired fluid flow which is in the memory, is introduced into the memory by the user, or is calculated by the controller from information supplied by the user. The controller controls the motor to the rate of reduction of the chamber volume from calculations of dσ/dt from $R_i$ and $S_R$ values associated with a series of specific chamber volumes σ. The $S_R$ values can be empirically determined, mathematically calculated, or calculated by a combination of empirical observations and mathematical calculations. A table similar to Table 2 can be prepared for $S_R$.

The inventive principles disclosed herein are applicable to a method as well as an apparatus. The method includes the steps of placing the flexible reservoir or bag in the chamber, determining within the controller, such as by electronically calculating, the volume of the chamber to be reduced dσ by the formula dσ=dV·$S_\sigma$ from values of dV and $S_\sigma$ in the memory as explained above, and electronically actuating the motor to reduce the chamber volume according to the $d\sigma$ calculation. This method allows for a controlled, relatively high precision delivery of fluid to a patient for varying volumes over time.

Similarly, the method of controlling the rates of delivery merely factors the time parameter into the volume control. The method includes the steps of placing the reservoir or bag 15 into the chamber, electronically calculating in the controller the rate the volume of the chamber is to be reduced by the formula $$\frac{d\sigma}{dt} = R_i \cdot S_R \qquad \text{(Eq. 16)}$$

from the values of $R_i$ and $S_R$ in the memory, and electronically activating the volume reducing means according to the calculation of the controller. This method allows for controlled, relatively high precision delivery of fluid to a patient for varying rates such as a ramp-up, constant rate and ramp-down commonly used for IV fluid infusion.

Figure 5:
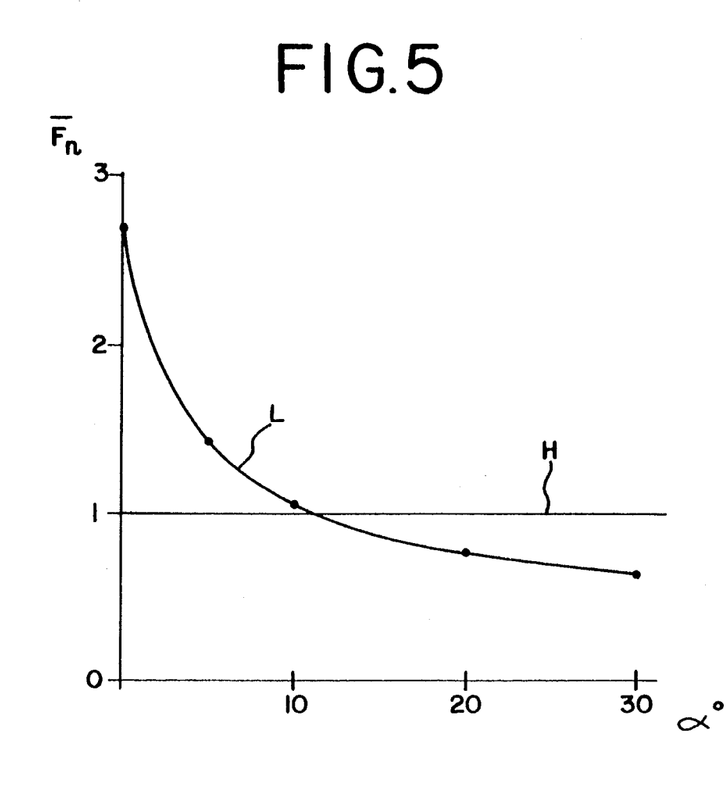
FIG. 5 is a graphic representation of a force ratio as a function of angular position of the moveable plate for the preferred embodiment.

FIG. 5 is a graph of force ratio $\overline{F}_n$ as it relates to the changing angular position of moveable plate 22. The x axis represents in degrees angle $\alpha$ of moveable plate 22 relative to front wall 12F, as shown in FIG. 4. The y axis represents force ratio $\overline{F}_n$, which is the ratio of $F_n$ to $F_y$. A plot of the values for $\overline{F}_n$ obtained above is shown by curved line L. Horizontal line H represents a value of 1, which reflects that $F_n = F_y$.

As shown in FIG. 5, when angle $\alpha$ between moveable plate 22 and front wall 12F is relatively large (i.e., 30°), $F_n > F_y$. As previously mentioned, however, when angle $\alpha$ is relatively large, the contact area between bag surface 34, moveable plate 22 and front wall 12F is relatively small, and the force necessary to express a predetermined volume out of bag 15 at a predetermined rate is also small.

As angle $\alpha$ decreases to about 12°, $F_n > F_y$ as shown by the intersection of curved line L and horizontal line H. As angle $\alpha$ decreases, the contact area between bag surface 34, moveable plate 22 and front wall 12F increases. As per the previous discussion, therefore, $F_n$ increases at a rate which corresponds to the increase in contact area.

Other arrangements of motor assembly 38 are possible within the scope of the present invention. For instance, motor assembly 38 may include a transmission or other gear train to divide down the incremental rotation of the motor assembly 38 into smaller increments of movement of lead screw 50.

Figure 6:
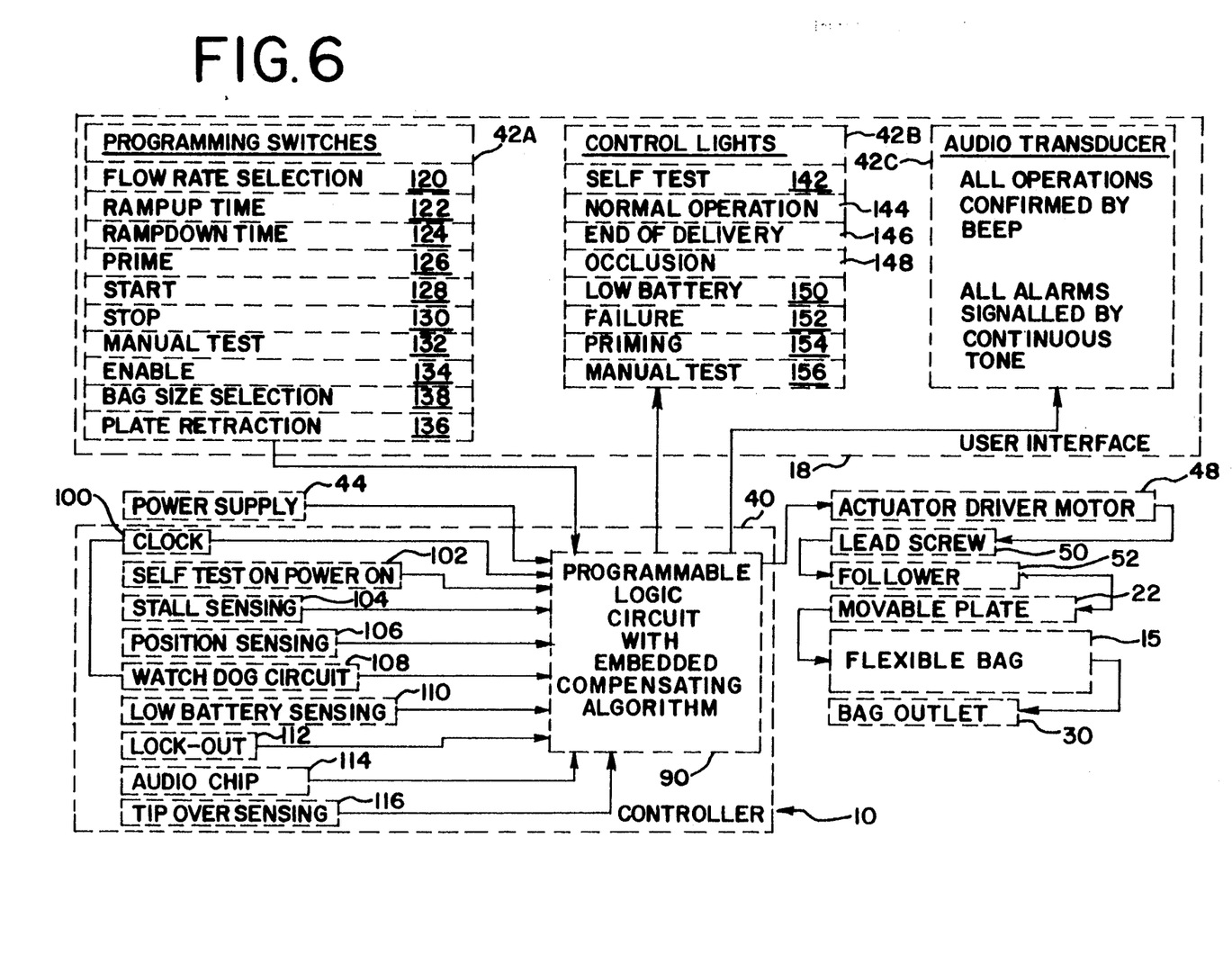
FIG. 6 is a diagrammatic representation of the control, input and output systems of the preferred embodiment.

FIG. 6 is a block diagram of pump system 10 of the present invention. Pump system 10, which in a preferred embodiment is a five volt circuitry on average, is energized by power supply 44. Power is preferably supplied by four AA batteries which, at the beginning of an IV delivery, provide six volts. Power supply 44 is electrically connected to controller 40. In the preferred embodiment, controller 40 includes programmable logic circuit (PLC) 90 (which implements the algorithms and logic necessary to control step pulse frequency as a function of the selected flow rate), clock 100, self test on power on circuit 102, stall sensing circuit 104, position sensing circuit 106, watch dog circuit 108, low battery sensing circuit 110, lock-out circuit 112, digitized audio chip 114, and tip over sensing switch 116.

Clock 100 is a standard quartz crystal oscillator commonly used in any logic circuitry. Clock 100 provides the time reference necessary for real time operation of PLC 90. Clock 100 also communicates with watch dog circuit 108, which ensures that PLC 90 is operating in response to clock signals of clock 100.

Self test on power on circuit 102 performs an automatic test of the electrical integrity of pump system 10. Self test circuit 102 ensures that all electrical input and output connections are intact when pump system 10 is energized. It also tests the electrical integrity of the circuitry of controller 40 and actuator driver motor 48.

Stall sensing circuit 104 senses current to motor 48 and provides an output signal in the event of an abrupt increase in current. In addition, stall sensing circuit 104 senses the back emf generated by motor 48. Stall sensing circuit 104, therefore, determines two elements. First, stall sensing circuit 104 detects any obstructions to fluid flow from bag 15. Stall sensing circuit 104 also determines any problems with motor drive assembly 38 itself. Any abrupt increases in current flow to motor 48 over a relatively short period of time, or any decrease in back emf results in an output signal which indicates pump system 10 is not operating properly.

Position sensing circuit 106 records the number of step pulse outputs to motor 48. Position sensing circuit 106 begins counting when the angular distance between moveable plate 22 and front wall 12F is at its greatest (i.e., step 0). The number of step pulse outputs from controller 40 to motor 48 corresponds to the number of steps of motor 48, which in turn relates to the angular distance traveled by moveable plate 22. For a uniform volume IV bag (e.g., three liters), the angular position of moveable plate 22 and the contact area between bag surface 34, moveable plate 22 and front wall 12F, are specific to the volume of fluid contained within bag 15.

Low battery sensing circuit 110 is a voltage comparator which measures the voltage of power supply 44 against a voltage referenced point, and cuts off power supply 44 if the voltage of power supply 44 falls below a predetermined level. In the preferred embodiment, the logic circuitry of controller 40 requires at least about 3.6 volts for proper operation. As such, low battery sensing circuit 110 insures accurate operation of the logic circuitry of controller 40 throughout operation of pump system 10.

Lock-out circuit 112 is provided to override the manual programming features of user interface 18. Lock-out circuit 112 allows a physician or other medical personnel to select certain programing parameters and then prevent a patient from altering those parameters.

Digital audio chip 114 carries prerecorded warning messages which, upon receiving input from the appropriate circuitry, are communicated via audio transducer 42C of user interface 18.

Tip over sensing circuit 116 is a position sensing circuit which shuts down pump system 10 in the event of any unusual or extreme orientations of pump system 10.

Controller 40 is programmable and receives inputs from and delivers outputs to user interface 18. As shown in FIG. 6, user interface 18 includes programing switches 42A, control lights 42B, and audio transducer 42C.

Switches 42A include flow rate selection switch 120, ramp-up time switch 122, ramp-down time switch 124, prime switch 126, start switch 128, stop switch 130, manual test switch 132, enable switch 134, plate retraction switch 136 and bag size selection switch 138.

Switches 120, 122, and 124 are usually set by the physician or other medical personnel attending to the programming of pump system 10. Flow rate switch 120 programs controller 40 to deliver IV fluid at a desired rate according the specific delivery needs of the patient.

Ramp-up time switch 122 and ramp-down time switch 124 serve to gradually increase and decrease, respectively, the IV fluid delivery to and from the predetermined flow rate to allow the patient's system to gradually adjust to the introduction and cessation of intravenous fluid.

Prime switch 126 is provided to completely charge catheter 16 with fluid and remove all air from catheter 16 and bag 15 before the delivery of IV fluid to the patient. Once all air has been expressed from catheter 16 and bag 15, prime switch 126 is manually opened. The delivery of IV fluid is then initiated by momentarily actuating enable switch 134 and start switch 128. Stop switch 130 is provided to allow the patient to interrupt delivery of IV fluid during the course of any IV delivery.

Manual test switch 132 is provided to allow a patient or attending physician to determine whether pump system 10 is operating properly. Enable switch 134 is a safety switch to ensure that no inadvertent activation of other switches occurs. In order to reprogram controller 40, enable switch 134 must be closed to alter flow rate selection switch 120, ramp-up time switch 122 or ramp-down time switch 124. Plate retraction switch 136 is provided to move moveable plate 22 to a starting position after the end of an IV delivery. Bag size selection switch 138 is provided in the event that a bag having a maximum size other than three liters is used in pump system 10. Activation of bag size selection switch 138 adapts PLC 90 to produce logic necessary to operate pump system 10 with the particular bag size selected.

Control lights 42B provide a visual indication of the operation of pump system 10. Control lights 42B include self test light 142, normal operation light 144, end of delivery light 146, occlusion light 148, low battery light 150, system failure light 152, priming light 154, and manual test light 156.

Self test light 142 is activated upon receiving input from self test on power on circuit 102, when circuit 102 is conducting a test of the integrity of pump system 10. Normal operation light 144 is continuously displayed throughout normal operation of pump system 10. End of delivery light 146 receives input from position sensing circuit 106, and indicates when the angular distance between moveable plate 22 and stationary side 24 is approximately zero degrees. At this position, the volume of bag chamber 20 and bag 15 is also approximately zero.

Occlusion light 148 receives input from stall sensing circuit 104 and is displayed whenever an abrupt increase in current is experienced over a relatively short period of time by stall sensing circuit 104. Low battery light 150 receives input from low battery sensing circuit 110 and is displayed when the voltage supplied by power supply 44 drops below about 3.6 volts. Failure light 152 is displayed in the event of any failure of pump system 10.

Priming display light 154 is displayed when prime switch 126 is closed and pump system 10 is being primed. Manual test light 156 is displayed when manual test switch 132 is closed and the manual test is being performed on pump system 10.

Controller 40 regulates and records step pulse outputs to motor 48, which in turn drives lead screw 50. As lead screw 50 rotates one revolution, follower 52 is linearly moved along lead screw 50 for a distance which relates to the rotational distance travelled by lead screw 50. The linear movement of follower 52 away from motor 48 causes push rod 54 to move moveable plate 22 towards stationary wall 24, thereby expressing fluid out of bag 15 and out bag outlet 30.

Pump system 10 of the present invention enables fluid contained in an IV bag which has a variable geometry to be delivered at a constant predetermined rate independent of variations of a pressure differential between an interior of the IV bag and the patient. Pump system 10 positively displaces a predetermined volume of fluid from the bag by decreasing the bag chamber volume at a rate which is adjusted according to an increase in the contact area between the bag surface and the surfaces of the bag chamber, the nonlinear relationship of reduced volume of the chamber to the reduced volume of the bag, or their respective rates of reduction. The relationship between the bag chamber volume and the IV bag volume is embodied in compensating algorithms in the control circuitry.

The use of simple programmable logic as the sole means for controlling motor 48 provides an inexpensive means for accurately delivering IV fluid at a constant predetermined rate. Due to the predictable relationships between the steps of motor 48, the angle between moveable plate 22 and front wall 12F, and the change of contact area between bag surface 34, moveable plate 22 and front wall 12F as a function of the angle $\alpha$, pump system 10 eliminates the need for complicated or expensive feedback sensors to monitor and control the rate of fluid flow out bag outlet 30. The ability to minimize components also enhances the dependability of pump system 10 and minimizes the chance of component failure which is inherent in pumps of the present art.

Figure 7:
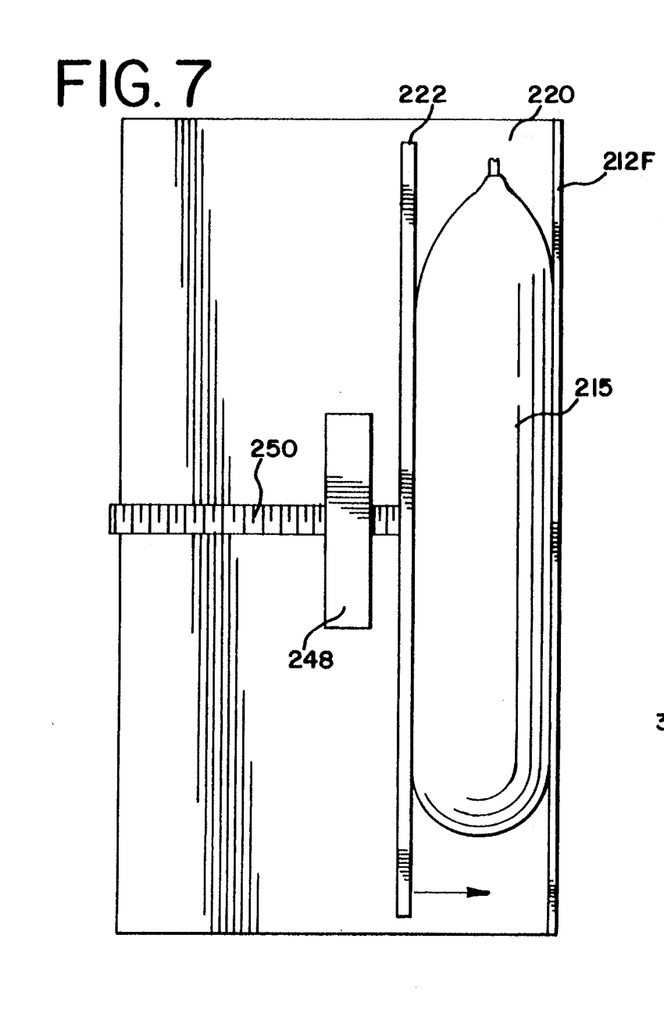
FIG. 7 is a elevational view of a first alternative embodiment of the present invention.

Many of the principles of the present invention are not limited to V-shaped chambers, but would be applicable to square or rectangular chambers, which use a moveable plate that is parallel to the opposing stationary wall. FIG. 7 illustrates a first alternative embodiment having moveable plate 22 and front or stationary wall 212F to define a rectangular chamber 220. The bag or flexible reservoir 215 is contacted and pressed by the moveable plate 222 which is moved toward the front wall 212F by motor 248 through lead screw 250. The general arrangement of remaining mechanical components is contemplated as shown in FIG. 2.

The motor 248 of this alternative embodiment communicates with a controller (not shown in FIG. 7, but corresponding to controller 40 in FIG. 2) which periodically turns the stepper motor 248 on and off to accomplish the desired fluid flow. The principles of the controller operation, calculation and actuation of the motor are consistent with the principles discussed above. Moreover, the general principles of the present invention may be applied to this arrangement to accomplish a relatively high precision, variable rate control of fluid pumping from the bag to a patient.

Figure 8:
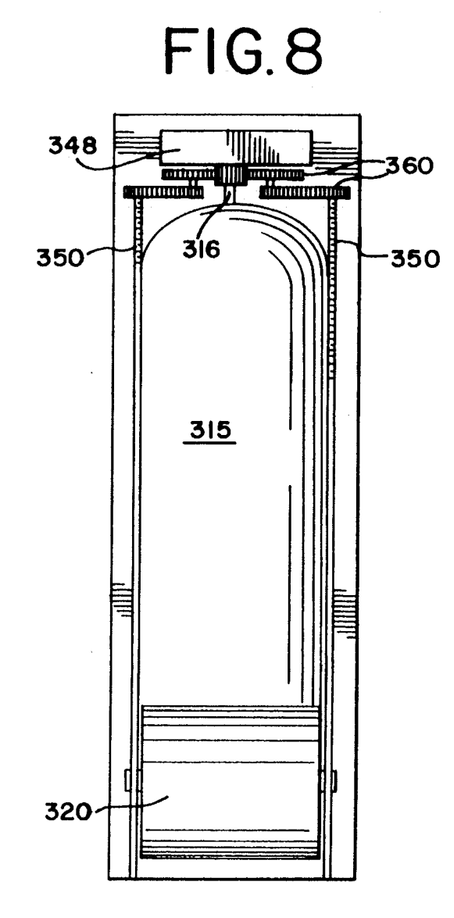
FIG. 8 is a top planar view of a second alternative embodiment of the present invention.

The principles of the present invention also are applicable to a roller-type pump. FIG. 8 shows a top planar view of the chamber portion of a second alternative embodiment of the present invention. The flexible bag 315 resides in a chamber between a roller 320 and the stationary wall, which initially contacts the lower part of the bag 315. At the opposite end of the roller is the catheter 316 which receives fluid from the bag 315. The roller is controllably moved along the bag toward catheter 316 to express fluid from the bag through the catheter 316. Lead screws 350 which communicate with either side of the roller 320 controllably move the roller along the bag when actuated by motor 348 through gearing 360.

Figure 9:
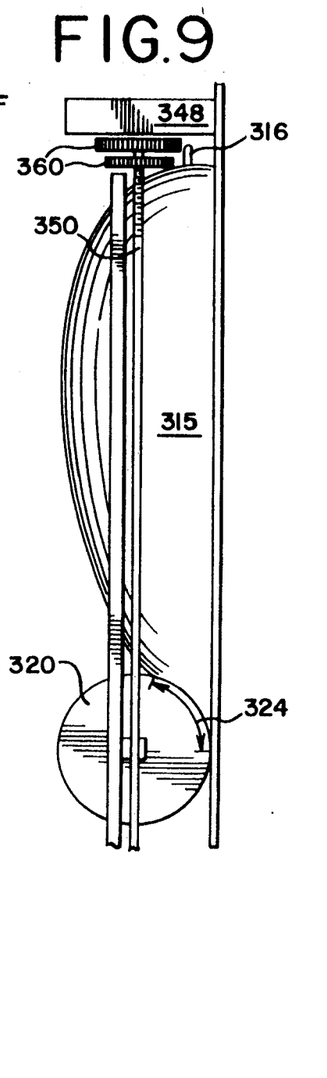
FIGS. 9, 10 and 11 are elevational views of the second alternative embodiment of FIG. 8, shown in time sequence as fluid is expressed from the bag.
Figure 10:
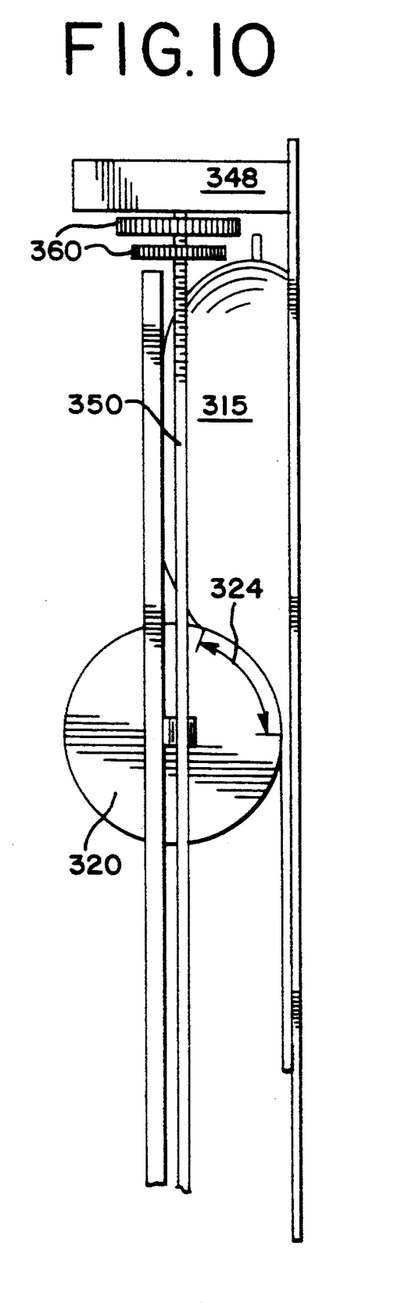
Figure 11:
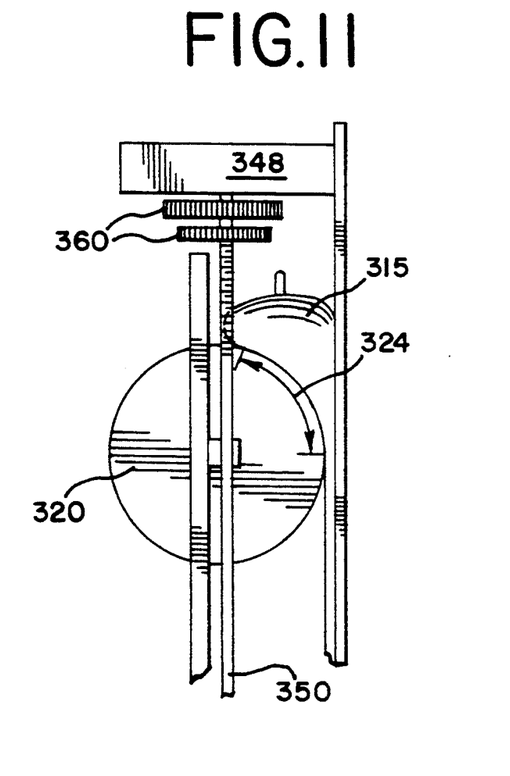

FIG. 9 is a elevational view of the same portion of the second alternative embodiment shown in FIG. 8. The surface of the roller 320 initially contacts the lower portion of the bag 315, as shown by arrows 324. As shown in FIGS. 10 and 11, the relationship of the surface of the roller changes as it progresses towards catheter 316 and the geometry of bag 315 changes. FIG. 10 shows the change in position of the roller relative to the bag, approximately halfway along its path.

FIG. 11 shows the further progress of the roller towards the catheter 316 side of the bag 315. The surface of roller 320 contacting the bag 315 changes as the roller proceeds from initially contacting the bag 315, to an intermediate position and then to the end position, near the catheter 316.

The second embodiment as shown in FIGS. 8–11 would include a general arrangement of remaining mechanical components as contemplated in FIG. 2 as would be appropriate for the roller-type pump. The controller (not shown in FIGS. 8–11 but corresponding to controller 40 in FIG. 2) periodically turns the stepper motor 348 on and off to accomplish the desired fluid flow. The principles of the controller operation, calculation and actuation of the motor are consistent with the principles discussed above with respect to the preferred embodiment.

In the preferred and alternative embodiments, bag chamber 20 is designed to accept standard-sized IV bags ranging in size from fifty milliliters to three liters. Portable infusion pumps known in the art typically use miniature dedicated fluid reservoirs, which requires that contents from a standard-sized IV bag be transferred to the dedicated fluid reservoir. The need to transfer IV bag contents from a standard IV bag to a nonstandard reservoir increases the likelihood that the contents may become contaminated. The ability of pump system 10 to use standard-sized IV bags eliminates double handling of the IV bag contents and the attendant likelihood of contamination. It also eliminates the substantial additional costs associated with dedicated disposable reservoirs used by portable infusion pumps of the present art.

The present invention contemplates an apparatus having low energy consumption and, consequently, reduced energy needs, decreased bulk and increased portability. The combination of a controller with a stepper motor having an iterative on/off, forward-only operation during infusion avoids the use of energy to constantly press against the bag for the maintenance of an equilibrium state. Also, because of the mechanical advantages and the controller control, small batteries provide sufficient power to run the pump, avoiding the necessity for AC power, large batteries or frequent replacement of batteries, which would make portability impractical. These principles can be applied to the preferred and the two alternative embodiments, but may be particularly applicable for the V-shaped chamber arrangement which provide the additional mechanical advantages discussed above, reducing still further the power requirements and increasing portability.

Although the present invention has been described with reference to preferred embodiments, workers skilled in the art will recognize that changes may be made in form and detail without departing from the spirit and scope of the invention.

What is claimed is:

1. An infusion pump for delivering a controlled rate of an intravenous fluid from a reservoir to a patient, the infusion pump comprising:
   a flexible, variable geometry reservoir containing intravenous fluid and having an outlet to allow the exit of fluid therefrom when the volume V of the reservoir is reduced;
   a chamber containing the reservoir and having initial volume greater than the reservoir, the chamber having volume $\sigma$ which can be reduced;
   means for reducing the chamber volume incrementally by $d\sigma$ and the volume of the reservoir therein incrementally by dV which is associated with $d\sigma$ at specific chamber volume $\sigma$; and
   programmable controller having a memory, the controller communicating with the chamber volume reducing means to control the rate of reduction of the chamber volume, wherein the controller, upon actuation, reduces the chamber volume according to the formula $$d\sigma = dV \cdot S_\sigma$$

where $S_\sigma$ is the previously determined relationship of reservoir volume reduction to chamber volume reduction at chamber volume $\sigma$, and wherein the controller controls $d\sigma$ by determinations from values of dV and $S_\sigma$ contained in the controller memory.

2. The infusion pump of claim 1 wherein $S_\sigma$ is empirically determined from measurements of the relationship of reservoir volume to chamber volume as the chamber volume is reduced.

3. The infusion pump of claim 1 wherein the chamber is comprised of at least a first wall and an opposing second wall, and wherein the chamber volume is reduced by movement of the first wall toward the second wall.

4. The infusion pump of claim 3 wherein the chamber volume reducing means comprises a motor in communication with the controller, and mechanical linkage means communicating between the motor and the first wall for moving the first wall toward the second wall.

5. The infusion pump of claim 1 wherein the variable geometry reservoir is a standard IV bag.

6. The infusion pump of claim 1 further comprising a housing suitable for portability, the housing containing the chamber, the reservoir, the chamber volume reducing means and the controller.

7. The infusion pump of claim 6 further comprising a power source contained within the housing and communicating with the controller and the chamber volume reducing means.

8. The infusion pump of claim 3 wherein the first wall has upper and lower ends and is pivotally connected at its lower end to the second wall.

9. The infusion pump of claim 3 wherein the first wall is parallel to the second wall and remains parallel during movement of the first wall relative to the second wall.

10. The infusion pump of claim 1 wherein the chamber volume reducing means comprises a roller which presses against the reservoir to reduce the effective volume of the chamber available to the reservoir.

11. The infusion pump of claim 4 wherein the chamber volume reducing means comprises:
- a stepper motor;
- a drive shaft which is rotated by the stepper motion;
- a follower engaging the drive shaft such that rotational movement of the shaft causes movement of the follower along the shaft; and
- a push rod communicating between the first wall and the follower.

12. An infusion pump for delivering a controlled rate of an intravenous fluid from a reservoir to a patient, the infusion pump comprising:
- a flexible, variable geometry reservoir containing intravenous fluid and having an outlet to allow exit of fluid therefrom when the volume V of the reservoir is reduced;
- a chamber containing the reservoir and having initial volume greater than the reservoir, the chamber having volume $\sigma$ which can be reduced;
- means for reducing the chamber volume incrementally by $d\sigma$ and the volume of the reservoir therein;
- a programmable controller having a memory, the controller communicating with the chamber volume reducing means to control the rate of reduction of the chamber volume, wherein the controller, upon actuation, reduces the chamber volume at a rate $$\frac{d\sigma}{dt} = R_i \cdot S_R$$

where $R_i$ is the incremental rate of intravenous fluid delivered to the patient associated with incremental chamber volume reduction $d\sigma$ and the time interval dt, and $S_R$ is the previously determined relationship of rate of chamber volume reduction to rate of fluid flow $R_i$ at chamber volume $\sigma$, and wherein the controller controls rate $d\sigma/dt$ by determinations from values of $R_i$ and $S_R$ contained in the controller memory.

13. The infusion pump of claim 12 wherein $S_R$ is empirically determined from measurements of the relationship of infusion rate $R_i$ to chamber volume reduction rate $d\sigma/dt$ at chamber volume $\sigma$.

14. The infusion pump of claim 12 wherein the chamber is comprised of a first wall and an opposing second wall, and wherein the chamber volume is reduced by movement of the first wall toward the second wall.

15. The infusion pump of claim 14 wherein the chamber volume reducing means comprises a motor in communication with the controller, and mechanical linkage means communicating between the motor and the first wall for moving the first wall toward the second wall.

16. The infusion pump of claim 12 wherein the variable geometry reservoir is a standard IV bag.

17. The infusion pump of claim 12 further comprising a housing suitable for portability, the housing containing the chamber, the reservoir, the chamber volume reducing means and the controller.

18. The infusion pump of claim 17 further comprising a power source contained within the housing and communicating with the chamber volume reducing means.

19. The infusion pump of claim 14 wherein the first wall has upper and lower ends and is pivotally connected at its lower end to the second wall.

20. The infusion pump of claim 14 wherein the first wall is parallel to the second wall and remains parallel during movement of the first wall relative to the second wall.

21. The infusion pump of claim 12 wherein the chamber volume reducing means comprises a roller which presses against the reservoir to reduce the effective volume of the chamber available to the reservoir.

22. The infusion pump of claim 15 wherein the chamber volume reducing means comprises:
- a stepper motor;
- a drive shaft which is rotated by the stepper motion;
- a follower engaging the drive shaft such that rotational movement of the shaft causes movement of the follower along the shaft; and
- a push rod communicating between the first wall and the follower.

* * * * *